US012728083B2

(12) United States Patent
Kajikawa et al.

(10) Patent No.: US 12,728,083 B2
(45) Date of Patent: Sep. 8, 2026

(54) 1,3-BUTYLENE GLYCOL PRODUCT

(71) Applicant: DAICEL CORPORATION, Osaka (JP)

(72) Inventors: Yasuteru Kajikawa, Tokyo (JP); Tetsuro Nakanishi, Tokyo (JP); Yuuichirou Hirai, Tokyo (JP); Keisuke Ono, Tokyo (JP); Midori Umehara, Tokyo (JP); Yuki Teshima, Tokyo (JP)

(73) Assignee: DAICEL CORPORATION, Osaka (JP)

( * ) Notice: Subject to any disclaimer, the term of this patent is extended or adjusted under 35 U.S.C. 154(b) by 1029 days.

(21) Appl. No.: 17/640,701

(22) PCT Filed: Sep. 3, 2020

(86) PCT No.: PCT/JP2020/033416
§ 371 (c)(1),
(2) Date: Mar. 4, 2022

(87) PCT Pub. No.: WO2021/045148
PCT Pub. Date: Mar. 11, 2021

(65) Prior Publication Data

US 2022/0323322 A1 Oct. 13, 2022

(30) Foreign Application Priority Data

Sep. 5, 2019 (JP) ................................ 2019-162351
Sep. 5, 2019 (JP) ................................ 2019-162352
Jan. 7, 2020 (JP) ................................ 2020-001084

(51) Int. Cl.
*A61K 8/34* (2006.01)
*A61Q 19/00* (2006.01)
*C07C 31/20* (2006.01)

(52) U.S. Cl.
CPC ........... *A61K 8/345* (2013.01); *A61Q 19/007* (2013.01); *C07C 31/207* (2013.01)

(58) Field of Classification Search
CPC ..... A61K 8/345; A61Q 19/007; C07C 31/207
See application file for complete search history.

(56) References Cited

U.S. PATENT DOCUMENTS 6,376,725 B1 4/2002 Tsuji et al.
2003/0018224 A1 1/2003 Tsuji et al.
2004/0254407 A1* 12/2004 Mizutani ................ C07C 29/80 568/852
2015/0298101 A1 10/2015 Tomishige et al.
2022/0290192 A1 9/2022 Burgard et al.

FOREIGN PATENT DOCUMENTS

CN 101665409 A 3/2010
CN 104651243 B 2/2018
EP 1211234 A2 6/2002
EP 1 437 337 A1 7/2004
EP 4026823 A1 7/2022
EP 4026824 A1 7/2022
JP 61-65834 A 4/1986
JP 7-258129 A 10/1995
JP 2001-213822 A 8/2001
JP 2001-213824 A 8/2001
JP 2001-213825 A 8/2001
JP 2001-213828 A 8/2001
JP 2001-288131 A 10/2001
JP 2012-525158 A 10/2012
JP 2016-160253 A 9/2016
KR 10-1575717 B1 12/2015
WO WO 00/07969 A1 2/2000

OTHER PUBLICATIONS

Extended European Search Report for European Application No. 20861663.1, dated Nov. 2, 2023.
European Communication pursuant to Rule 114(2) EPC for European Application No. 20861663.1, dated Nov. 8, 2024.
English translation of International Preliminary Report on Patentability and Written Opinion mailed Mar. 17, 2022, in PCT/JP2020/033416.
International Search Report mailed Oct. 13, 2020, in PCT/JP2020/033416.
U.S. Appl. No. 17/640,514, filed Mar. 4, 2022.
U.S. Appl. No. 17/640,387, filed Mar. 4, 2022.
“1,3-Butylene glycol-P,” Safety Data Sheet, Aug. 25, 2000, pp. 1-8, with English translation.
“1.3 Butanediol (for cosmetics) [13BGUK],” Website of Daicel Corporation, Dec. 10, 2021, 2 pages total, with English translation.

(Continued)

*Primary Examiner* — Sikarl A Witherspoon
(74) *Attorney, Agent, or Firm* — Morgan, Lewis & Bockius LLP

(57) ABSTRACT

Provided is a high-purity 1,3-butylene glycol product that is colorless and odorless, and furthermore, unlikely to be colored over time. A 1,3-butylene glycol product, having, according to a gas chromatographic analysis performed under predetermined conditions, a peak area ratio of 1000 ppm or lower appearing in a relative retention time ranging from 2.3 to 2.4, provided that the relative retention time for a peak of 1,3-butylene glycol is 1.0.

14 Claims, 3 Drawing Sheets

(56) References Cited

OTHER PUBLICATIONS

"Catalog of Hi-Sugar Cane BG," Ecocert, Jun. 1, 2007, 2 pages total, with partial English translation.
"Hi-Sugar Cane BG," Safety Data Sheet, Apr. 23, 2007, pp. 1-7, with English translation.
Certified Experiment Results, Dec. 20, 2021, 48 pages total, with English translation.
Description of Evidence, Dec. 20, 2021, pp. 1-2, with English translation.
Japanese Written Opposition for Japanese Patent No. 6890708, dated Dec. 20, 2021, with English translation.
Office Action issued in corresponding European Patent Application No. 20861663.1, dated Jul. 8, 2025.
Wang et al., "Heterogeneous Ceria Catalyst with Water-Tolerant Lewis Acidic Sites for One-Pot Synthesis of 1,3-Diols via Prins Condensation and Hydrolysis Reactions", Journal of the American Chemical Society, vol. 135, 2013, pp. 1506-1515.
Office Action issued in corresponding Korean Patent Application No. 10-2024-7022081, dated Oct. 23, 2025.

* cited by examiner

1,3-BUTYLENE GLYCOL PRODUCT

TECHNICAL FIELD

The present disclosure relates to a 1,3-butylene glycol product. The present application claims priority from the Japanese Patent Application No. 2019-162351 and the Japanese Patent Application No. 2019-162352, both filed in Japan on Sep. 5, 2019, and the Japanese Patent Application No. 2020-001084, filed in Japan on Jan. 7, 2020, the entire contents of which are incorporated herein by reference.

BACKGROUND ART 1,3-Butylene glycol is a colorless, transparent, and odorless liquid and has properties, such as low volatility, low toxicity, and high hygroscopicity, and has excellent chemical stability. 1,3-butylene glycol has a wide range of applications, including raw materials for various synthetic resins and surfactants, as well as materials for cosmetics, hygroscopic agents, high boiling point solvents, and antifreezes, etc. Particularly in recent years, 1,3-butylene glycol has been attracting attention for having excellent properties as a moisturizer, and demand is growing in the cosmetic industry.

1,3-butylene glycol obtained by a known manufacturing method have sometimes had an odor due to effects from by-products. In addition, 1,3-butylene glycol transparent immediately after production may be colored over time, which is a problem in storing for a long period of time.

For example, during use and/or storage after use of a cosmetic, the cosmetic is exposed to air. In addition, in manufacturing cosmetics, the manufacturing work is usually performed in air atmosphere, and the product may be heated for the purposes of, for example, sterilization. When 1,3-butylene glycol obtained by a known method is used in cosmetics, sometimes coloration occurs in the presence of air or by effects of heating. To solve such problems, removing by-products from crude 1,3-butylene glycol to obtain high-purity 1,3-butylene glycol has been required.

For a method to obtain high-purity 1,3-butylene glycol, a method has been proposed, in which sodium hydroxide is added to crude 1,3-butylene glycol obtained by hydrogen reduction of an acetaldol and distillation is performed. In addition, other methods have been proposed, including a method in which an alkali metal base is added to crude 1,3-butylene glycol from which a high boiling point product has been removed, the mixture is heat-treated, then 1,3-butylene glycol is distilled, and the alkali metal compound and a high boiling point product are separated as residues, and subsequently a low boiling point product is distilled off from the 1,3-butylene glycol distillate (Patent Documents 1 to 6). Various methods for purifying 1,3-butylene glycol have been thus proposed to obtain high-purity 1,3-butylene glycol.

CITATION LIST

Patent Document

Patent Document 1: JP 07-258129 A
Patent Document 2: WO 00/07969
Patent Document 3: JP 2001-213822 A
Patent Document 4: JP 2001-213824 A
Patent Document 5: JP 2001-213825 A
Patent Document 6: JP 2001-213828 A

SUMMARY OF INVENTION

Technical Problem

However, 1,3-butylene glycol products obtained from these purification methods still contain by-products and have a problem of having an odor and also a problem of being colored over time.

Thus, an object of the present disclosure is to provide a high-purity 1,3-butylene glycol product that is colorless and odorless, and furthermore, unlikely to be colored over time.

Solution to Problem

As a result of diligent research to achieve the above object, the inventors of the present disclosure found that improving the manufacturing method of crude 1,3-butylene glycol provides a high-purity 1,3-butylene glycol product that is odorless and colorless, and furthermore, unlikely to be colored over time. The present disclosure was completed based on these findings.

That is, the present disclosure provides a 1,3-butylene glycol product, having, according to a gas chromatographic analysis performed under conditions set forth below:

a peak area ratio of 1000 ppm or lower appearing in a relative retention time ranging from 2.3 to 2.4, provided that the relative retention time for a peak of 1,3-butylene glycol is 1.0:

in which the conditions for the gas chromatographic analysis are as follows:

Analytical Column: a column with dimethylpolysiloxane as a stationary phase, having a length of 30 m, an inner diameter of 0.25, and a film thickness of 1.0 μm Heating Conditions: heating from 80° C. to 120° C. at 5° C./min, then heating again to 160° C. at 2° C./min and maintaining for 2 minutes, and further heating to 230° C. at 10° C./min and maintaining at 230° C. for 18 minutes Sample Introduction Temperature: 250° C.

Carrier Gas: helium

Column Gas Flow Rate: 1 mL/min

Detector and Detection Temperature: a flame ionization detector (FID), 280° C.

For the 1,3-butylene glycol product, a Hazen color number (APHA) after keeping 180° C. for 3 hours in air atmosphere is preferably 60 or less.

1,3-butylene glycol in the 1,3-butylene glycol product is preferably a reduced form of at least one compound selected from the group consisting of acetaldol, paraldol, and aldoxane.

In addition, the present disclosure also provides a moisturizer containing the 1,3-butylene glycol product.

Furthermore, the present disclosure also provides a cosmetic product containing the moisturizer.

Advantageous Effects of Invention

The 1,3-butylene glycol product of the present disclosure is colorless and transparent and less likely to be colored over time, and thus is suitably used for applications, such as cosmetics and moisturizers.

DESCRIPTION OF EMBODIMENTS

Figure 1:
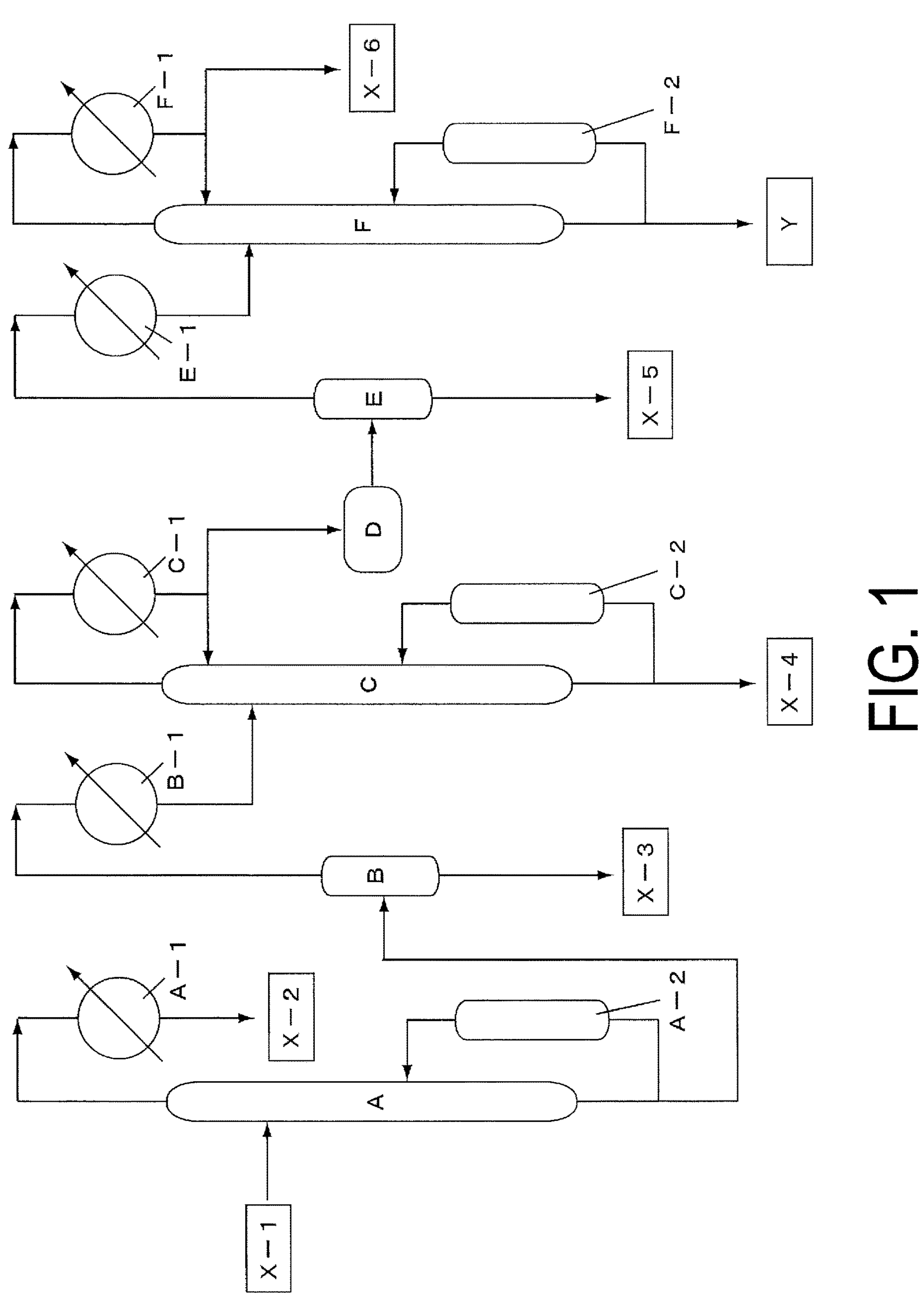
FIG. 1 is a flowchart showing a manufacturing method (purification method) for a 1,3-butylene glycol product of the present disclosure.

A 1,3-butylene glycol product of the present disclosure is characterized by having, according to a gas chromatographic analysis performed under conditions set forth below, a peak area ratio of 1000 ppm or lower appearing in a relative retention time ranging from 2.3 to 2.4, provided that the relative retention time for a peak of 1,3-butylene glycol is 1.0.

The conditions for the gas chromatographic analysis are as follows:

Analytical Column: a column with dimethylpolysiloxane as a stationary phase, having a length of 30 m, an inner diameter of 0.25 mm, and a film thickness of 1.0 μm Heating Conditions: heating from 80° C. to 120° C. at 5° C./min, then heating again to 160° C. at 2° C./min, and maintaining for 2 minutes, and further heating to 230° C. at 10° C./min and maintaining at 230° C. for 18 minutes Sample Introduction Temperature: 250° C.

Carrier Gas: helium

Column Gas Flow Rate: 1 mL/min

Detector and Detection Temperature: a flame ionization detector (FID), 280° C.

The peak area ratio is, for example, preferably 500 ppm or lower, more preferably 250 ppm or lower, even more preferably 150 ppm or lower, still more preferably 100 ppm or lower, particularly preferably 50 ppm or lower, and most preferably 20 ppm or lower. In the present disclosure, the "(peak) area ratio" means a ratio of the area of a specific peak relative to the sum of the areas of all peaks appearing in the chromatogram. In addition, all peaks mean, for example, all of the peaks appearing in the analysis continued until and discontinued at a relative retention time of 7.8, provided that the relative retention time of 1,3-butylene glycol is 1.0. With the area ratio of the above peak in the above ranges, the generation of odor and coloration over time tend to be reduced.

Examples of a component corresponding to the peak appearing in the relative retention time ranging from 2.3 to 2.4, provided that the relative retention time of the peak of 1,3-butylene glycol is 1.0, in the gas chromatographic analysis under the above conditions include an acetal of 1,3-butylene glycol and acetaldol. The acetal is a by-product with a higher boiling point than that of 1,3-butylene glycol. That is, the 1,3-butylene glycol product of the present disclosure preferably has a low content of the acetal as a by-product.

In the 1,3-butylene glycol product of the present disclosure, the peak area ratio of 1,3-butylene glycol in the gas chromatographic analysis of the above conditions is, for example, preferably 99.5% or higher, more preferably 99.7% or higher, even more preferably 99.8% or higher, and particularly preferably 99.9% or higher. With the area ratio of the above peak in the above ranges, the generation of odor and coloration over time tend to be reduced.

In the 1,3-butylene glycol product of the present disclosure, in the gas chromatographic analysis under the above conditions, the peak area ratio appearing in the relative retention time ranging from 1.6 to 1.8, provided that the relative retention time for the peak of 1,3-butylene glycol is 1.0, is, for example, preferably 2000 ppm or lower, more preferably 1000 ppm or lower, even more preferably 600 ppm or lower, and particularly preferably 200 ppm or lower. With the area ratio of the above peak in the above ranges, the generation of odor and coloration over time tend to be reduced. The lower limit of the area ratio may be, for example, 10 ppm, 20 ppm, 50 ppm, or 100 ppm.

Examples of a component corresponding to the peak appearing in a relative retention time ranging from 1.6 to 1.8 in the gas chromatographic analysis under the above conditions include, provided that the relative retention time of the peak of 1,3-butylene glycol is 1.0, a hydride of a trimer of a raw material, which is aldehyde. That is, the 1,3-butylene glycol product of the present disclosure preferably has a low content of the hydride as a by-product.

A Hazen color number (APHA) after the 1,3-butylene glycol product of the present disclosure is kept at 180° C. for 3 hours in air atmosphere is not particularly limited but is, for example, preferably 60 or less, more preferably 40 or less, and even more preferably 30 or less. In addition, an APHA after keeping 100° C. for 75 days in air atmosphere is not particularly limited but is preferably 40 or less, more preferably 30 or less, even more preferably 20 or less, and particularly preferably 15 or less. For both APHAs described above, the lower limit may be, for example, 1, 3, 5, or 10.

An APHA of the 1,3-butylene glycol product of the present disclosure (APHA of the 1,3-butylene glycol product not stored at high temperature) is not particularly limited but is, for example, preferably 20 or less, more preferably 10 or less, and even more preferably 5 or less. The lower limit of the APHA may be, for example, 1 or 2.

For the APHA of the 1,3-butylene glycol product of the present disclosure, a ratio of the APHA after keeping 180° C. for 3 hours to the APHA before keeping, that is [(APHA after keeping 180° C. for 3 hours)/(APHA before keeping)], is not particularly limited but is preferably 15 or lower and more preferably 12 or lower. In addition, the ratio is 1 or higher, or may be 2 or higher or 5 or higher.

For the APHA of the 1,3-butylene glycol product of the present disclosure, a ratio of the APHA after keeping 100° C. for 75 days to the APHA before keeping, that is [(APHA after keeping 100° C. for 75 days)/(APHA before keeping)], is not particularly limited but is preferably 10 or lower and more preferably 7 or lower. In addition, the ratio is 1 or higher, or may be 2 or higher.

Examples of the 1,3-butylene glycol in the 1,3-butylene glycol product of the present disclosure include (1) a reduced form of an acetaldol, (2) a hydrolyzate of 1,3-butylene oxide, (3) a selective hydrocracked product of erythritol, (4) a selective water adduct to butadiene, (5) a hydride of n-butanol-3-one, (6) a hydride of 1-butanol-3-one, (7) a hydride of 3-hydroxy-1-butanoic acid, (8) a hydride of β-butyrolactone, and (9) a hydride of diketen. The 1,3-butylene glycol of the present disclosure may be one or a mixture of two or more of the above (1) to (9).

The 1,3-butylene glycol in the 1,3-butylene glycol product of the present disclosure is preferably (1) a reduced form of an acetaldol. In addition, from the viewpoint of the yield of 1,3-butylene glycol, the reduced form of an acetaldol is preferably a liquid-phase reduced form of an acetaldol. The reasons for this are that an acetaldol has a high boiling point, that an acetaldol is unstable to heat and readily undergoes a dehydration reaction at high temperatures to become crotonaldehyde or the like, and furthermore, that the reaction rate of the dehydration reaction is higher than that of the reduction reaction (hydrogenation reaction) at high temperatures. That is, when an acetaldol is subjected to vapor-phase reduction, the temperature inside the reaction system needs to be increased to high temperature, but subjecting an acetaldol to high temperature causes a dehydration reaction to produce crotonaldehyde or the like, and the subsequent reduction reaction produces by-products, such as butanol. Thus, this results in relatively reduced yield of the target 1,3-butylene glycol. Thus, to obtain a high-purity 1,3-butylene glycol product, a liquid phase reduction rather than a gas phase reduction is preferably performed. Here, 1,3-butylene glycol as a reduced form of an acetaldol can also be referred to as 1,3-butylene glycol obtained by a method of hydrogen reduction of an acetaldol. Similarly, 1,3-butylene glycol as a liquid-phase reduced form of an acetaldol can also be referred to as 1,3-butylene glycol obtained by a method of hydrogen reduction of an acetaldol in a liquid phase. In addition, 1,3-butylene glycol as a hydrolysate of 1,3-butylene oxide can also be referred to as 1,3-butylene glycol obtained by hydrolyzing 1,3-butylene oxide.

In general, in manufacturing 1,3-butylene glycol, by-products are produced in the manufacturing process. For example, in manufacturing 1,3-butylene glycol by hydrogen reduction of an acetaldol, acetaldehyde; butylaldehyde; crotonaldehyde; acetone; a low boiling point product (low boiling point compound) having an unsaturated bond, such as methyl vinyl ketone; a condensate of these; a condensate of 1,3-butylene glycol and the above low boiling point product (e.g., an acetal of 1,3-butylene glycol and acetaldol); or the like is produced as a by-product. Furthermore, in addition to the above, an acetal of crotonaldehyde and 1,3-butylene glycol; an acetal of acetaldehyde and 1,3-butylene glycol; an acetal of a hydride of a trimer of acetaldol, acetaldehyde, and acetaldehyde; or the like is produced as a by-product.

In addition, these by-products have properties as a color-causing substance or an odor-causing substance. Whether the acetal is a color-causing substance or an odor-causing substance is uncertain, and the acetal is also considered to have both properties. Specifically, the acetal itself is unlikely to be an odor-causing substance but can form an odor-causing substance by a change over time or heating. Furthermore, the acetal may be hydrolyzed to form acetaldol, which is an odor-causing substance and has an oxidation (coloration) promoting effect. Thus, the acetal can also be said to be a color-causing substance. Here, the color-causing substance is defined as including not only a substance actually having a hue itself but also a substance changing over time into a substance having a hue. In addition, the odor-causing substance is defined as including not only a substance actually emitting an odor itself but also a substance changing over time into a substance emitting an odor.

These by-products, especially the acetal described above, are difficult to completely remove even using a purification means, such as distillation known in the art. This is considered to be because crude 1,3-butylene glycol is subjected to high temperature conditions and alkali treatment in the purification stage of the crude 1,3-butylene glycol, and new by-products are produced accordingly. Thus, as described above, the 1,3-butylene glycol products of Patent Documents 1 to 6 contain many by-products and thus have an odor, and furthermore, are colored over time. Thus, it can be said that to obtain a high-purity 1,3-butylene glycol product, only improving the method for purifying crude 1,3-butylene glycol is insufficient, and improving the method of manufacturing crude 1,3-butylene glycol itself is necessary.

For the manufacturing of 1,3-butylene glycol, a raw material for hydrogenation containing an acetaldol is used. The acetaldol is any compound that becomes 1,3-butylene glycol by hydrogenation reduction and is not particularly limited, but examples include acetoaldol; its cyclic dimer paraaldol; aldoxane, a cyclic trimer of a type of acetaldehyde; and mixtures of these.

The method of manufacturing the acetaldol (e.g., acetaldol or paraldol) is not particularly limited, but the acetaldol may be, for example, those obtained by an aldol condensation reaction of acetaldehyde in the presence of a basic catalyst or those obtained by pyrolysis or the like of aldoxane. A reaction crude liquid obtained by the reaction described above and containing an acetaldol may be neutralized with an acid and used in the manufacturing of 1,3-butylene glycol. Such a reaction crude liquid may contain, in addition to an acetaldol, acetaldehyde, crotonaldehyde, another aldehyde component; a low boiling point product; a high boiling point product, such as an aldehyde dimer or trimer; water; a salt; and the like. In the present specification, a compound with a lower boiling point than that of 1,3-butylene glycol may be referred to as a "low boiling point product", and a compound with a higher boiling point than that of 1,3-butylene glycol may be referred to as a "high boiling point product".

The reaction crude liquid may be subjected to a pretreatment, such as dealcoholization distillation, dehydration distillation, desalting, or impurity removal, as necessary, and a product obtained by removing by-products, such as unreacted acetaldehyde and crotonaldehyde, may be used. Examples of the pretreatment method include distillation, adsorption, ion exchange, conversion to a high boiling point product by heating, and decomposition. For the distillation, a distillation method of various types, such as reduced pressure, normal pressure, increased pressure, azeotropic, extraction, or reaction, can be used.

The content of the acetaldol in the raw material for hydrogenation is not particularly limited but is, for example, preferably 50 wt. % or higher (e.g., from 50 to 99 wt. %), more preferably 60 wt. % or higher (e.g., from 60 to 98 wt. %), even more preferably from 65 to 98 wt. %, particularly preferably from 80 to 95 wt. %, and most preferably from 85 to 95 wt. %. With the content of the acetaldol within the above ranges, impurities contained in crude 1,3-butylene glycol tend to be reduced.

The raw material for hydrogenation may or may not contain water but preferably contains water from the viewpoint of the purity of 1,3-butylene glycol product. The water content in the raw material for hydrogenation is not particularly limited but is, for example, preferably 2 wt. % or higher, more preferably 5 wt. % or higher, even more preferably 10 wt. % or higher, and particularly preferably 15 wt. % or higher. The upper limit may be, for example, 50 wt. %, 40 wt. %, or 35 wt. %. With the water content within the above ranges, the acetal of 1,3-butylene glycol and acetaldol contained in the resulting crude 1,3-butylene glycol is decreased, and thus this tends to increase the purity of the 1,3-butylene glycol product finally obtained. This is because the raw material for hydrogenation contains water to a certain extent, and the acetal is hydrolyzed into 1,3-butylene glycol accordingly as well as coexisting acetaldol is reduced into 1,3-butylene glycol.

Hereinafter, the method of manufacturing crude 1,3-butylene glycol will be described. The present manufacturing method is characterized by reducing a raw material for hydrogenation containing an acetaldol in the presence of a hydrogenation catalyst to obtain crude 1,3-butylene glycol.

Examples of the hydrogenation catalyst include Raney nickel. The hydrogenation catalyst can be used by suspending or filling but is preferably used by suspending. The amount of the hydrogenation catalyst to be used is not particularly limited but is, for example, preferably from 1 to 30 parts by weight, more preferably from 4 to 25 parts by weight, even more preferably from 8 to 20 parts by weight, and particularly preferably from 12 to 18 parts by weight relative to 100 parts by weight of the raw material for hydrogenation. The amount of hydrogen to be used in the reduction reaction is not particularly limited but is, for example, preferably from 0.5 to 40 parts by weight, more preferably from 1 to 30 parts by weight, even more preferably from 4 to 20 parts by weight, and particularly preferably from 8 to 12 parts by weight relative to 100 parts by weight of the raw material for hydrogenation. The pressure (total pressure) in the reaction system in the reduction reaction is not particularly limited but is, for example, preferably from 150 to 500 atm, more preferably from 180 to 450 atm, even more preferably from 200 to 400 atm, and particularly preferably from 250 to 350 atm. The ratio of the hydrogen pressure (partial pressure of hydrogen) to the total pressure in the reaction system is not particularly limited but is, for example, preferably 80% or higher (from 80 to 100%), more preferably from 85 to 99.9%, even more preferably from 90 to 99.5%, and particularly preferably from 95 to 99% of the total pressure. The hydrogen pressure (partial pressure of hydrogen) in the reaction system is not particularly limited but is, for example, preferably from 100 to 500 atm, more preferably from 150 to 450 atm, even more preferably from 150 to 400 atm, and particularly preferably from 200 to 350 atm. The reaction temperature in the reduction reaction is not particularly limited but is, for example, preferably from 110 to 140° C. and more preferably from 120 to 140° C. The reaction time (residence time) in the reduction reaction is not particularly limited but is, for example, preferably from 30 to 300 minutes, more preferably from 80 to 280 minutes, and even more preferably from 120 to 250 minutes.

With the amount of the hydrogenation catalyst and the hydrogen amount to be used in the reduction reaction, the hydrogen pressure, reaction temperature, and reaction time (residence time) in the reduction reaction within the above ranges, the reaction rate (hydrogenation rate) from the acetaldol to 1,3-butylene glycol is improved. Thus, for example, this tends to decrease the acetalization reaction of 1,3-butylene glycol and acetaldol and to produce a high-purity 1,3-butylene glycol product of the present disclosure. This tendency is strongly affected especially by the hydrogen pressure in the reduction reaction. That is, with the hydrogen pressure in the reduction reaction within the above ranges, the reaction rate (reduction rate) from the acetaldol to 1,3-butylene glycol is significantly improved, and this consequently decreases the acetal of 1,3-butylene glycol and acetaldol and results in producing a high-purity 1,3-butylene glycol product of the present disclosure. The present reaction can be carried out in any of a batch, semi-batch, or continuous manner.

The crude 1,3-butylene glycol obtained by the hydrogen reduction of the raw material for hydrogenation can be obtained as a 1,3-butylene glycol product, for example, by undergoing dehydration, desalting, distillation for removing a high boiling point product, an alkaline reaction, dealkalization, and distillation.

The content ratio of a high boiling point product in the crude 1,3-butylene glycol is not particularly limited but is, for example, preferably from 0.1 to 20 wt. %, more preferably from 1 to 15 wt. %, and even more preferably from 2 to 10 wt. %. With the content ratio of a high boiling point product in the crude 1,3-butylene glycol within the above ranges, the amount of by-product contained in the 1,3-butylene glycol product finally obtained tends to be reduced.

The content ratio of a high boiling point product in the crude 1,3-butylene glycol after the distillation of a high boiling point product is 1.0 wt. % or lower and preferably 0.5 wt. % or lower. Using crude 1,3-butylene glycol with a low content of a high boiling point product eliminates or extremely reduces the production of a low boiling point product due to a decomposition reaction of the high boiling point product even when the crude 1,3-butylene glycol is heat-treated together with a base in the alkaline reaction. This results in a tendency to obtain an extremely high-quality 1,3-butylene glycol product that is not colored, and furthermore, less likely to be colored over time.

FIG. 1 is a flow sheet of an apparatus illustrating an example of an embodiment for obtaining a 1,3-butylene glycol product of the present disclosure. A is a dehydration column and is related to the dehydration. B is a desalting column and is related to the desalting. C is a distillation column for removing a high boiling point product and is related to the distillation for removing a high boiling point product. D is an alkaline reactor and is related to the alkaline reaction. E is a dealkalization column and is related to the dealkalization. F is a product distillation column and is related to the distillation. A-1, B-1, C-1, E-1, and F-1 are condensers. A-2, C-2, and F-2 are reboilers. Hereinafter, an example of an embodiment for obtaining the 1,3-butylene glycol product of the present disclosure is described using the present flow sheet.

Crude 1,3-butylene glycol (corresponding to "X-1") obtained by hydrogen reduction of a raw material for hydrogenation is fed to the dehydration column A. In the dehydration column A, water is distilled off from the top of the column by distillation, and from the bottom of the column is obtained a crude 1,3-butylene glycol stream containing 1,3-butylene glycol. The crude 1,3-butylene glycol stream is fed to the desalting column B. In the desalting column B, a crude 1,3-butylene glycol stream after the desalting is obtained from the top of the column, and from the bottom of the column is discharged a salt, a high boiling point product, or the like.

The crude 1,3-butylene glycol stream after the desalting described above is fed to the distillation column C for removing a high boiling point product. In the distillation column C for removing a high boiling point product, a high boiling point product is discharged from the bottom of the column. On the other hand, from the top of the column is obtained a crude 1,3-butylene glycol stream after the removal of a high boiling point product. The crude 1,3-butylene glycol distilled with the distillation column C for removing a high boiling point product is fed to the alkaline reactor (e.g., a flow-through tubular reactor) D and is treated with a base. In the alkaline reactor D or its upper stream, a base is added in 0.05 to 10 wt. % or preferably in 0.1 to 1.0 wt. % relative to the crude 1,3-butylene glycol stream after the removal of a high boiling point product. With the added amount of the base exceeding 10 wt. %, the base would precipitate in the distillation column, piping, or the like, and this would tend to cause blockage. In addition, the decomposition reaction of a high boiling point compound would occur, tending to produce a by-product on the contrary. With the added amount of less than 0.05 wt. %, the effect of decomposing by-products is reduced, and thus neither of these are preferred.

The base added in the alkaline reactor D or its upper stream is not particularly limited but is, for example, preferably an alkali metal compound. Examples of the alkali metal compound include sodium hydroxide, potassium hydroxide, sodium (bi)carbonate, and potassium (bi)carbonate, but from the viewpoint of reducing by-products contained in the 1,3-butylene glycol product finally obtained, sodium hydroxide or potassium hydroxide is preferred. The base may be added as is in the solid form but is preferably added in an aqueous solution to facilitate operation and contact with a target solution. One of the bases described above may be used alone, or two or more may be used simultaneously.

The reaction temperature in the alkaline reactor D is not particularly limited but is, for example, preferably from 90 to 140° C. and more preferably from 110 to 130° C. This is because the reaction at a reaction temperature lower than 90° C. would require long reaction residence time and thus require a reactor with a large volume and make the process uneconomical, and the reaction at a rection temperature exceeding 140° C. would increase coloration in the 1,3-butylene glycol product finally obtained. The reaction residence time is, for example, preferably from 5 to 120 minutes and more preferably from 10 to 30 minutes. This is because with a reaction residence time shorter than 5 minutes, the reaction would be insufficient and thus deteriorate the quality of the 1,3-butylene glycol product finally obtained, and the reaction with a reaction residence time exceeding 120 minutes would require a large reactor and increase the cost of equipment, and thus would be disadvantageous from the economic point of view.

After exiting the alkaline reactor D, the reaction crude stream is fed to the dealkalization column (a thin film evaporator) E, and the base and the like are removed from the bottom of the column by evaporation. On the other hand, from the top of the dealkalization column E is obtained a crude 1,3-butylene glycol stream after the removal of a base. The evaporator used for the dealkalization column E is suitably a natural downward flow thin-film evaporator or a forced-stirring thin-film evaporator with a short residence time for the purpose of reducing the thermal history to the process fluid.

Evaporation is performed in the evaporator used for the dealkalization column E, for example, under a reduced pressure at the top of the column of 100 toff or lower and preferably from 5 to 20 torr. The temperature of the evaporator is, for example, preferably from 90 to 120° C. The crude 1,3-butylene glycol stream containing a low boiling point product distilled from the top of the column is fed to the product distillation column F.

Examples of the product distillation column F include perforated-plate columns and bubble columns, but more preferred is a packed column with a low pressure loss, filled with Sulzer Packing, Melapack (trade names of Sumitomo Heavy Industries, Ltd.), or the like. This is because 1,3-butylene glycol would be thermally decomposed at a high temperature (e.g., 150° C. or higher) and produce a low boiling point product, which is a coloring component, and thus the distillation temperature is to be lowered. In addition, this is also because a long thermal history (residence time) for 1,3-butylene glycol would also have a similar effect. Thus, the reboiler employed is preferably one with a short residence time of the process side fluid, for example, a thin-film evaporator, such as a natural downward flow thin-film evaporator or a forced-stirring thin-film evaporator.

When the concentration of a low boiling point product in a liquid to be charged is 5 wt. % or lower, the product distillation column F preferably has a number of theoretical plates, for example, from 10 to 20 stages. The liquid to be charged is preferably fed to a position from 20 to 70% of the height of the column from the top of the column. For the distillation in the product distillation column F, the pressure at the top of the column is, for example, preferably 100 torr or lower and more preferably from 5 to 20 torr. The reflux ratio is, for example, preferably from 0.5 to 2.0.

In FIG. 1, in charging to the product distillation column F, the column top vapor from the dealkalization column E is condensed in the condenser E-1, and the resulting condensed liquid is fed, but the column top vapor from the dealkalization column E may be directly fed to the product distillation column F. In the product distillation column F, an impurity, such as a low boiling point product, is distilled off from the top of the column, and 1,3-butylene glycol as a product is obtained from the bottom of the column of the product distillation column F (corresponding to "Y").

Moisturizer and Cosmetic Product

A moisturizer of the present disclosure contains the 1,3-butylene glycol product described above. Thus, the moisturizer has excellent moisturizing performance and has no coloring or odor, and is unlikely to be colored over time, and furthermore, is unlikely to increase acid concentration over time also in a state containing water. The moisturizer of the present disclosure may contain a component other than the 1,3-butylene glycol product described above, such as a moisturizer component other than the 1,3-butylene glycol product described above. In the moisturizer of the present disclosure, the content of the 1,3-butylene glycol product described above is, for example, 10 wt. % or higher, preferably 30 wt. % or higher, more preferably 50 wt. % or higher, even more preferably 80 wt. % or higher, and particularly preferably 90 wt. % or higher, and the moisturizer may be composed of only the 1,3-butylene glycol product described above.

A cosmetic of the present disclosure contains the moisturizer described above. The blending amount of the 1,3-butylene glycol product in the cosmetic product of the present disclosure is any amount in which the moisturizing performance can be exhibited according to the type and form of cosmetic. The blending amount of the 1,3-butylene glycol product in the cosmetic product of the present disclosure is, for example, from 0.01 to 40 wt. %, preferably from 0.1 to 30 wt. %, more preferably from 0.2 to 20 wt. %, even more preferably from 0.5 to 15 wt. %, and particularly preferably from 1 to 10 wt. %.

The cosmetic product of the present disclosure may contain, in addition to the 1,3-butylene glycol product, for example, another moisturizer; an oil, such as a vegetable oil, a hydrocarbon oil, a higher fatty acid, a higher alcohol, or a silicone; a surfactant, such as an anionic surfactant, a cationic surfactant, an amphoteric surfactant, or a nonionic surfactant; a preservative, a sequestrant, a thickener, a powder, an ultraviolet absorber, an ultraviolet blocker, a fragrance, or a pH adjuster; or a medicinal ingredient or bioactive component, such as a vitamin preparation, a skin activator, a blood circulation promoter, a skin-lightening preparation, an antibacterial agent, or an anti-inflammatory agent.

The cosmetic product of the present disclosure can be a skin cosmetic product, such as a lotion, an emulsion, a cream, a gel, a pack, or a mask; or a hair cosmetic product, such as a shampoo, a rinse, or a hair restorer. In addition, the cosmetic product can be a sunscreen cosmetic product or a make-up cosmetic product. Furthermore, the cosmetic product can be a pharmaceutical product or quasi drug containing a medical component.

The cosmetic product of the present disclosure can be manufactured by a method known per se.

EXAMPLES

Hereinafter, the present disclosure will be described more specifically with reference to examples, but the present disclosure is not limited by these examples. "Parts" used in the examples means "parts by weight" unless otherwise specified.

Example 1

The method of manufacturing 1,3-butylene glycol will be described using FIG. 1.

Relative to 100 parts of an acetaldol solution containing 30 wt. % of water (mixed solution of 70 parts of acetaldol and 30 parts of water) as a raw material, 10 parts of hydrogen were charged in a reactor for liquid-phase hydrogenation reduction, and 15 parts of Raney nickel were added as a catalyst. The reactor was kept at 135° C. and 300 atm, and liquid-phase hydrogenation reduction was performed. After the catalyst was separated, the liquid after the reaction was neutralized with sodium hydroxide, alcohols were removed, and crude 1,3-butylene glycol (1) was obtained.

The crude 1,3-butylene glycol (1) (corresponding to "X-1" in FIG. 1) was charged in the dehydration column A. In the dehydration column A, water was extracted from the top of the column, and 15 parts of fresh water were added as reflux water relative to 100 parts of the charged liquid amount. The pressure was adjusted to 50 torr, and crude 1,3-butylene glycol (2) containing 0.5 wt. % or lower of water was obtained from the bottom of the column. The water extracted from the top of the column was discharged (corresponding to "X-2" in FIG. 1).

The crude 1,3-butylene glycol (2) was then charged in the desalting column B. In the desalting column B, a salt, a high boiling point product, and a portion of 1,3-butylene glycol were discharged as the evaporation residue from the bottom of the column (corresponding to "X-3" in FIG. 1). The discharge amount of the evaporation residue was 5 parts relative to 100 parts of the charged liquid amount. On the other hand, from the top of the column was obtained crude 1,3-butylene glycol (3) containing 1,3-butylene glycol, a low boiling point product, and a portion of a high boiling point product.

The crude 1,3-butylene glycol (3) was then charged in the distillation column C for removing a high boiling point product. In the distillation column C for removing a high boiling point product, a high boiling point product and a portion of 1,3-butylene glycol were discharged from the bottom of the column (corresponding to "X-4" in FIG. 1). The discharge amount was 20 parts relative to 100 parts of the charged liquid amount. On the other hand, from the top of the column were obtained 80 parts of crude 1,3-butylene glycol (4) containing a low boiling point product. The crude 1,3-butylene glycol (4) was then charged in the alkaline reactor D. At this time, a 10 wt. % sodium hydroxide aqueous solution was added to give a concentration of sodium hydroxide of 0.2 wt. % relative to the charged liquid. The reaction temperature was maintained at 120° C. in the alkaline reactor D, and a reaction was performed at a residence time of 20 minutes.

A reaction crude liquid exiting the alkaline reactor D was then charged in the dealkalization column E. In the dealkalization column E, sodium hydroxide, a high boiling point product, and a portion of 1,3-butylene glycol were discharged from the bottom of the column (corresponding to "X-5" in FIG. 1). The discharge amount was 10 parts relative to 100 parts of the charged liquid amount. On the other hand, from the top of the column were obtained 90 parts of crude 1,3-butylene glycol (5) containing 1,3-butylene glycol and a low boiling point product.

The crude 1,3-butylene glycol (5) was then charged in the product distillation column F. In the product distillation column F, 10 parts of a low boiling point product and a portion of 1,3-butylene glycol relative to 100 parts of the charged liquid amount were distilled off from the top of the column (corresponding to "X-6" in FIG. 1), and from the bottom of the column were obtained 90 parts of a 1,3-butylene glycol product (corresponding to "Y" in FIG. 1).

As a result of a gas chromatographic analysis performed under conditions described later on the 1,3-butylene glycol product described above, peaks in the relative retention time ranging from 2.3 to 2.4 were not higher than the detection limit (10 ppm or lower). In addition, the area ratio of peaks appearing in the relative retention time ranging from 1.6 to 1.8 was 130 ppm. A color aging test 1 was performed and revealed that the APHA after keeping 180° C. for 3 hours in air atmosphere was 21. Furthermore, a color aging test 2 was performed and revealed that the APHA after keeping 100° C. for 75 days in air atmosphere was 10. The APHA before performing these tests was 2. Furthermore, the score of an odor test was 1.

Comparative Example 1

As a result of a gas chromatographic analysis performed under conditions described later on 1,3-butylene glycol (product number: 13BGO) available from Daicel Corporation, the area ratio of peaks appearing in the relative retention time ranging from 2.3 to 2.4 was 1137 ppm. In addition, the area ratio of peaks appearing in the relative retention time ranging from 1.6 to 1.8 was 1010 ppm. A color aging test 1 was performed and revealed that the APHA after keeping 180° C. for 3 hours in air atmosphere was 80. Furthermore, a color aging test 2 was performed and revealed that the APHA after keeping 100° C. for 75 days in air atmosphere was 46. The APHA before performing these tests was 4. Furthermore, the score of an odor test was 2.

Gas Chromatographic Analysis

Figure 2:
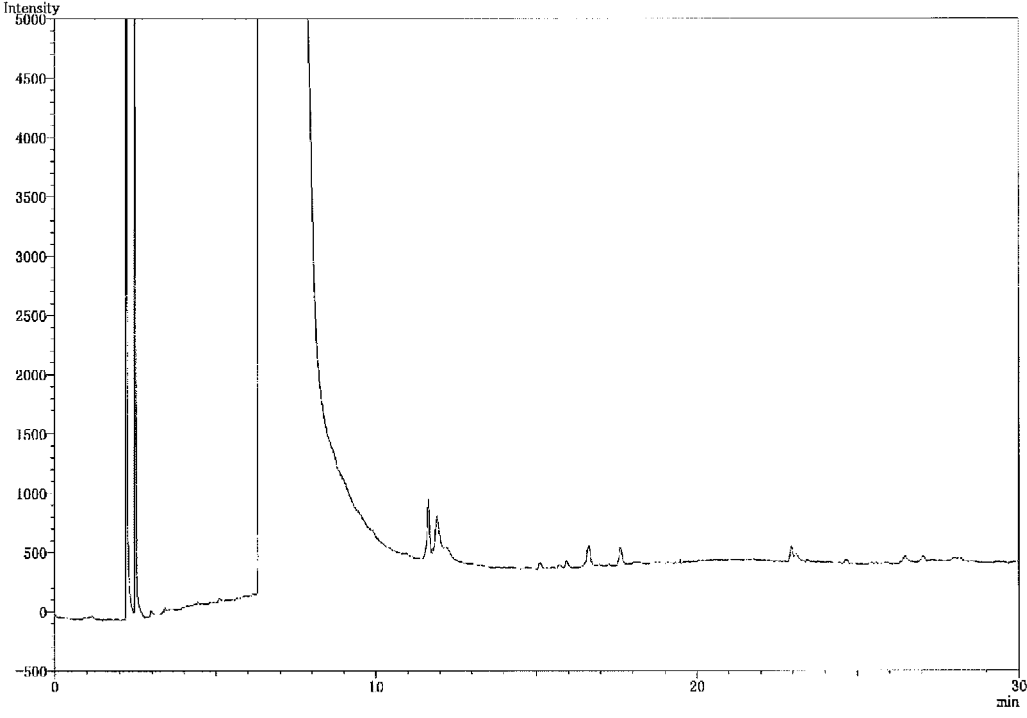
FIG. 2 is a chromatogram showing a gas chromatographic analysis for a 1,3-butylene glycol product in Example 1.
Figure 3:
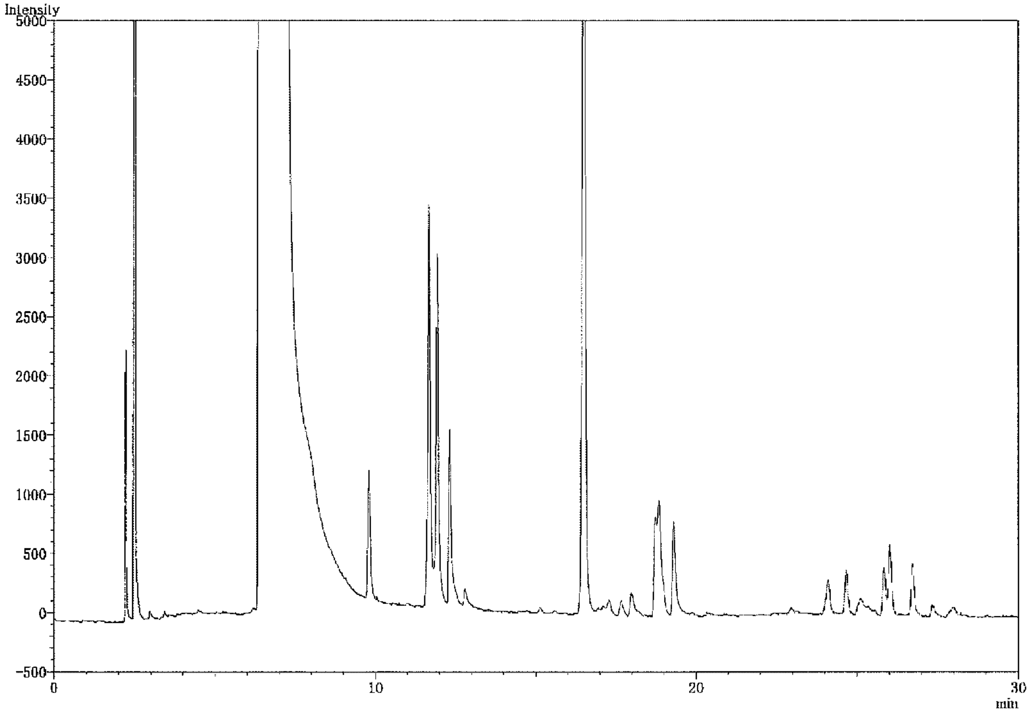
FIG. 3 is a chromatogram showing a gas chromatographic analysis for a 1,3-butylene glycol product in Comparative Example 1.

A gas chromatographic analysis of the target 1,3-butylene glycol product was performed under the conditions below. A chromatogram of the gas chromatographic analysis of 1,3-butylene glycol in Example 1 is shown in FIG. 2. In addition, a chromatogram of the gas chromatographic analysis of 1,3-butylene glycol in Comparative Example 1 is shown in FIG. 3.

Conditions for the gas chromatographic analysis:

Analytical Instrument: Shimadzu GC 2010

Analytical Column: Agilent J&W GC column—DB-1 (a column with dimethylpolysiloxane as a stationary phase, having a length of 30 m, an inner diameter of 0.25 mm, and a film thickness of 1.0 μm, available from Agilent Technologies Japan, Ltd.)

Heating Conditions: heating from 80° C. to 120° C. at 5° C./min, then heating again to 160° C. at 2° C./min and maintaining for 2 minutes, and further heating to 230° C. at 10° C./min and maintaining at 230° C. for 18 minutes.

Sample Introduction and Temperature: split sample introduction, 250° C.

Gas Flow Rate of Split and Carrier Gas: 23 mL/min, helium

Column Gas Flow Rate and Carrier Gas: 1 mL/min, helium

Detector and Temperature: a flame ionization detector (FID), 280° C.

Injection Sample: 0.2 μL of a 80 wt. % 1,3-butylene glycol product aqueous solution Color Aging Test 1

The target 1,3-butylene glycol product was placed in a wide-mouth bottle, the bottle was stoppered tightly and kept in a constant temperature oven set at 180° C. for 3 hours. A Hazen color number (APHA) of the 1,3-butylene glycol product after keeping was measured using a color difference meter ("ZE6000" available from Nippon Denshoku Industries Co., Ltd.) and a quartz cell with an optical path length of 10 mm.

Color Aging Test 2

The target 1,3-butylene glycol product was placed in a wide-mouth bottle, and the bottle was stoppered tightly and kept in a constant temperature oven set at 100° C. for 75 days. A Hazen color number (APHA) of the 1,3-butylene glycol product after keeping was measured using a color difference meter ("ZE6000" available from Nippon Denshoku Industries Co., Ltd.) and a quartz cell with an optical path length of 10 mm.

Odor Test

The target 1,3-butylene glycol product (100 mL) was placed in a wide-mouth reagent bottle (internal volume: 100 mL), and the bottle was stoppered tightly and allowed to stand at room temperature for about 120 minutes. Then, the stopper was opened, the content was transferred to a 300-mL wide-mouth beaker, and 100 mL of pure water was added into the beaker to make a total of 200 mL. The wide-mouth beaker was shaken with a hand to stir the content, and the odor was immediately smelled and scored according to the following evaluation.

1: Odor is not sensed

2: Slightly odorous

Hereinafter, variations of the invention according to the present disclosure will be described.

(1) A 1,3-butylene glycol product, having, according to a gas chromatographic analysis performed under conditions set forth below:

a peak area ratio of 1000 ppm or lower appearing in a relative retention time ranging from 2.3 to 2.4, provided that the relative retention time for a peak of 1,3-butylene glycol is 1.0:

in which the conditions for the gas chromatographic analysis are as follows:

Analytical Column: a column with dimethylpolysiloxane as a stationary phase, having a length of 30 m, an inner diameter of 0.25 mm, and a film thickness of 1.0 μm Heating Conditions: heating from 80° C. to 120° C. at 5° C./min, then heating again to 160° C. at 2° C./min and maintaining for 2 minutes, and further heating to 230° C. at 10° C./min and maintaining at 230° C. for 18 minutes Sample Introduction Temperature: 250° C.

Carrier Gas: helium

Column Gas Flow Rate: 1 mL/min

Detector and Detection Temperature: a flame ionization detector (FID), 280° C.

(2) The 1,3-butylene glycol product according to (1), having the peak area ratio appearing in the range from 2.3 to 2.4 is 500 ppm or lower, 250 ppm or lower, 150 ppm or lower, or 100 ppm or lower, 50 ppm or lower, or 20 ppm or lower.

(3) The 1,3-butylene glycol product according to (1) or (2), in which a component corresponding to the peak appearing in the range from 2.3 to 2.4 contains an acetal of 1,3-butylene glycol and acetaldol.

(4) The 1,3-butylene glycol product according to any one of (1) to (3), in which the peak area ratio of 1,3-butylene glycol in the gas chromatographic analysis under the conditions is 99.5% or higher, 99.7% or higher, 99.8% or higher, or 99.9% or higher.

(5) The 1,3-butylene glycol product according to any one of (1) to (4), having, according to the gas chromatographic analysis performed under the above conditions, a peak area ratio appearing in a relative retention time ranging from 1.6 to 1.8, provided that the relative retention time for the peak of 1,3-butylene glycol is 1.0, is 2000 ppm or lower, 1000 ppm or lower, 600 ppm or lower, or 200 ppm or lower, and a lower limit of the area ratio is 10 ppm, 20 ppm, 50 ppm, or 100 ppm.

(6) The 1,3-butylene glycol product according to (5), in which a component corresponding to the peak appearing in the range from 1.6 to 1.8 contains a hydride of a trimer of a raw material, which is acetaldehyde.

(7) The 1,3-butylene glycol product according to any one of (1) to (6), in which a Hazen color number (APHA) after keeping 180° C. for 3 hours in air atmosphere is 60 or less, 40 or less, or 30 or less, and a lower limit is 1, 3, 5, or 10.

(8) The 1,3-butylene glycol product according to any one of (1) to (7), in which an APHA after keeping 100° C. for 75 days in air atmosphere is 40 or less, 30 or less, 20 or less, or 15 or less, and a lower limit is 1, 3, 5, or 10.

(9) The 1,3-butylene glycol product according to any one of (1) to (8), in which an APHA is 20 or less, 10 or less, or 5 or less, and a lower limit is 1 or 2.

(10) The 1,3-butylene glycol product according to any one of (1) to (9), in which a ratio of the APHA after keeping 180° C. for 3 hours to the APHA before keeping, that is [(APHA after keeping 180° C. for 3 hours)/(APHA before keeping)], is 15 or lower or 12 or lower and 1 or higher, 2 or higher, or 5 or higher.

(11) The 1,3-butylene glycol product according to any one of (1) to (10), in which a ratio of the APHA after keeping 100° C. for 75 days to the APHA before keeping, that is [(APHA after keeping 100° C. for 75 days)/(APHA before keeping)], is 10 or lower or 7 or lower and 1 or higher or 2 or higher.

(12) The 1,3-butylene glycol product according to any one of (1) to (11), which is a reduced form of an acetaldol.

(13) The 1,3-butylene glycol product according to any one of (1) to (12), in which 1,3-butylene glycol in the 1,3-butylene glycol product is a reduced form of at least one compound selected from the group consisting of acetaldol, paraldol, and aldoxane.

(14) A moisturizer containing the 1,3-butylene glycol product described in any one of (1) to (13).

(15) A cosmetic product containing the moisturizer described in (14).

REFERENCE SIGNS LIST

A: Dehydration column

B: Desalting column

C: Distillation column for removing a high boiling point product

D: Alkaline reactor

E: Dealkalization column

F: Product distillation column

A-1, B-1, C-1, E-1, F-1: Condenser

A-2, C-2, F-2: Reboiler
X-1: Crude 1,3-butylene glycol
X-2: Water (discharged water)
X-3: A salt, a high boiling point product, and a portion of 1,3-butylene glycol
X-4: A high boiling point product and a portion of 1,3-butylene glycol
X-5: Sodium hydroxide, a high boiling point product, and a portion of 1,3-butylene glycol
X-6: A low boiling point product and a portion of 1,3-butylene glycol
Y: 1,3-butylene glycol product

INDUSTRIAL APPLICABILITY

The 1,3-butylene glycol product of the present disclosure is colorless and transparent and less likely to be colored over time, and thus is suitably used for applications, such as cosmetics and moisturizers.

The invention claimed is:

1. A 1,3-butylene glycol product, having, according to a gas chromatographic analysis performed under conditions set forth below:

1000 ppm or lower of an area ratio of a peak appearing in a relative retention time ranging from 2.3 to 2.4, provided that the relative retention time for a peak of 1,3-butylene glycol is 1.0, wherein a component corresponding to the peak appearing in the range from 2.3 to 2.4 contains an acetal of 1,3-butylene glycol and acetaldol, wherein the 1,3-butylene glycol product is obtained by reducing a raw material for hydrogenation containing acetaldols and water, wherein a content of the water in the raw material for hydrogenation is from 2 to 50 wt %, and wherein the conditions for the gas chromatographic analysis are as follows:

Analytical Column: a column with dimethylpolysiloxane as a stationary phase, having a length of 30 m, an inner diameter of 0.25 mm, and a film thickness of 1.0 μm Heating Conditions: heating from 80° C. to 120° C. at 5° C./min, then heating again to 160° C. at 2° C./min and maintaining for 2 minutes, and further heating to 230° C. at 10° C./min and maintaining at 230° C. for 18 minutes Sample Introduction Temperature: 250° C.

Carrier Gas: helium

Column Gas Flow Rate: 1 mL/min

Detector and Detection Temperature: a flame ionization detector (FID), 280° C.

2. The 1,3-butylene glycol product according to claim 1, wherein a Hazen color number (APHA) after keeping 180° C. for 3 hours in air atmosphere is 60 or less.

3. The 1,3-butylene glycol product according to claim 1, wherein 1,3-butylene glycol in the 1,3-butylene glycol product is a reduced form of at least one compound selected from the group consisting of acetaldol, paraldol, and aldoxane.

4. A moisturizer comprising the 1,3-butylene glycol product described in claim 1.

5. A cosmetic product comprising the moisturizer described in claim 4.

6. The 1,3-butylene glycol product according to claim 2, wherein 1,3-butylene glycol in the 1,3-butylene glycol product is a reduced form of at least one compound selected from the group consisting of acetaldol, paraldol, and aldoxane.

7. A moisturizer comprising the 1,3-butylene glycol product described in claim 2.

8. A moisturizer comprising the 1,3-butylene glycol product described in claim 3.

9. A moisturizer comprising the 1,3-butylene glycol product described in claim 6.

10. A cosmetic product comprising the moisturizer described in claim 7.

11. A cosmetic product comprising the moisturizer described in claim 8.

12. A cosmetic product comprising the moisturizer described in claim 9.

13. The 1,3-butylene glycol product according to claim 1, having greater than 0 ppm and not more than 1000 ppm of the area ratio of a peak appearing in the relative retention time ranging from 2.3 to 2.4.

14. The 1,3-butylene glycol product according to claim 1, wherein a peak area ratio of 1,3-butylene glycol in the gas chromatographic analysis under the conditions is 99.5% or higher.

* * * * *